United States Patent [19]

Hissung

[11] Patent Number: 4,787,744
[45] Date of Patent: Nov. 29, 1988

[54] CELL ARRANGEMENT AND CELL HOLDER FOR RECEIVING THE CELL ARRANGEMENT IN A SINGLE ORIENTATION

[75] Inventor: Alfred R. Hissung, Marburg-Marbach, Fed. Rep. of Germany

[73] Assignee: Behringwerke Antiengesellschart, Marburg, Fed. Rep. of Germany

[21] Appl. No.: 818,763

[22] Filed: Jan. 14, 1986

[30] Foreign Application Priority Data

Jan. 16, 1985 [DE] Fed. Rep. of Germany ... 8500884[U]

[51] Int. Cl.4 .................... G01N 1/10; G01N 21/03
[52] U.S. Cl. .................................................. 356/246
[58] Field of Search ................ 356/244, 246, 440; 250/576

[56] References Cited

U.S. PATENT DOCUMENTS 3,375,934 10/1965 Bates .................................. 356/244
4,251,159 2/1981 White ................................. 356/246
4,608,231 8/1986 Witty et al. ........................ 356/246

FOREIGN PATENT DOCUMENTS 0114056 7/1984 European Pat. Off. .
2435317 2/1975 Fed. Rep. of Germany .
2819820 11/1978 Fed. Rep. of Germany .
0218042 10/1985 Japan .................................. 356/244
84/02775 7/1984 World Int. Prop. O. .

Primary Examiner—Vincent P. McGraw
Assistant Examiner—S. A. Turner
Attorney, Agent, or Firm—Finnegan, Henderson, Farabow, Garrett & Dunner

[57] ABSTRACT

In this cell arrangement for optical investigations, the individual cells (1) are arranged in strips. They are held at different spacings from one another by connecting elements (2,5,12). The cell holder (9) associated therewith is provided with cell wells (11), which are disposed in a row and the spacings of which correspond to those of the cells.

5 Claims, 1 Drawing Sheet

CELL ARRANGEMENT AND CELL HOLDER FOR RECEIVING THE CELL ARRANGEMENT IN A SINGLE ORIENTATION

BACKGROUND OF THE INVENTION

The invention relates to a cell arrangement for optical investigations, with a cell holder to receive the cells.

DESCRIPTION OF THE RELATED ART

Cell arrangements of the kind mentioned are known from German OffenLegungsschrift No. 2,435,317. It is a disadvantage of this arrangement that individual cells, which are connected with one another by webs, are disposed relative to one another in such a manner that they cannot be inserted into a cell holder in an unambiguously defined configuration. Instances of interchange are accordingly not ruled out, that is, the cells may be inserted into the cell holder in an improper sequence since each cell will fit in more than one cell of the cell holder.

SUMMARY OF THE INVENTION

There accordingly exists the object of providing a cell arrangement with which it can be ensured that the individual cells are always received by the cell holder only in one and the same sequence.

The object is fulfilled by a cell arrangement, wherein the cells are arranged in strips, in which the individual cells are kept at different spacings from one another by connecting elements and the cell holder is provided with cell wells, which are disposed in sequence and the spacings of which correspond to those of the cells.

The connecting elements can consist of a frame provided with apertures, the apertures having different spacings. However, the connecting elements can also consist of webs of different width. The webs can exhibit predetermined breaking points, and can be disposed parallel to the longitudinal axis of the cell. The cell wells can be provided with arrangements for heating and cooling the cells.

BRIEF DESCRIPTION OF THE DRAWINGS

The invention is explained in greater detail hereinbelow with reference to drawings, which represent only a single embodiment. In the drawings.

DESCRIPTION OF THE PREFERRED EMBODIMENT

Figure 1:
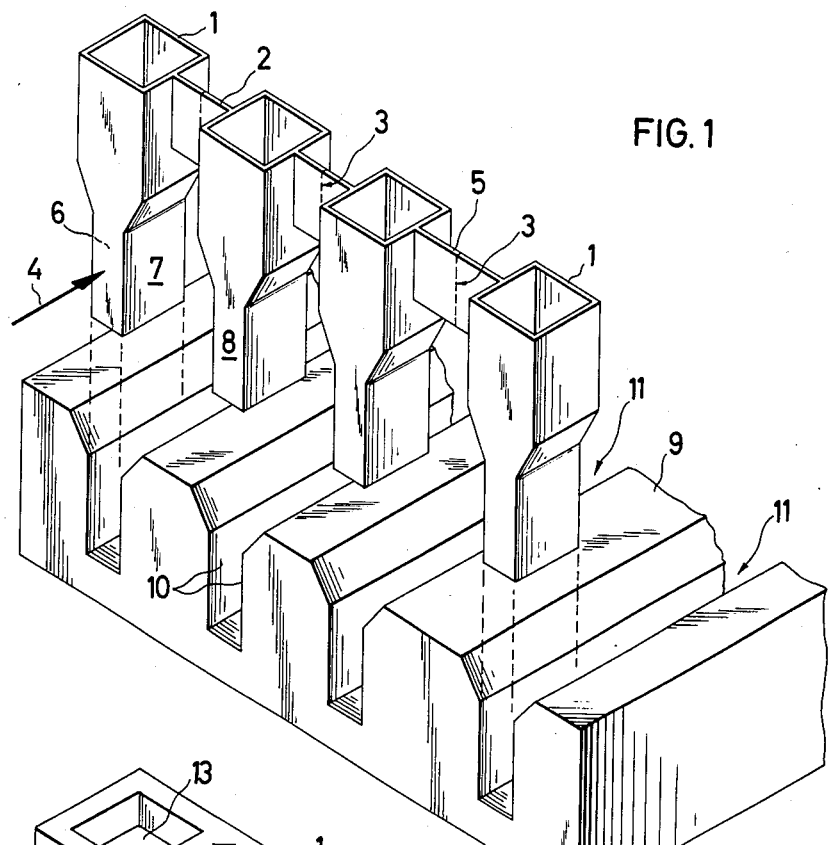
FIG. 1 shows the individual cells arranged in strips, together with the cell holder associated therewith.

The cell arrangement consists of the individual cells 1 and the cell holder 9. The cells 1 are arranged in strips and are held at different spacings from one another by connecting elements 2, 5 and 12 respectively. As is shown in FIG. 1, the connecting elements can consist of webs 2, 5 of different widths. The webs 2, 5 can be provided with predetermined breaking lines 3. As shown in FIG. 1, these can be disposed centrally in the web, but also in the region of the web which borders on the cell. The webs can be displaced parallel to the longitudinal axis of the cell, but also perpendicular thereto (not shown). The cell holder is provided with cell wells 11, which are disposed in sequence and the spacings of which correspond to those of the cells. In order to facilitate the insertion of the cells into and the removal thereof from the cell wells 11, it can be expedient to incline the lateral walls 10 of the latter and the lateral walls 6 and 7 of the cell 1 slightly in relation to one another. The optical windows are designated by 8, and the direction of irradiation by 4.

Figure 2:
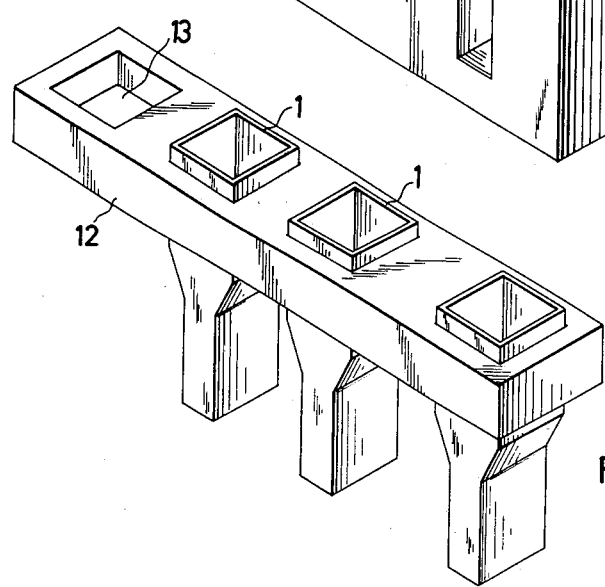
FIG. 2 shows a further embodiment of the cells arranged in strips.

In the variant according to FIG. 2, the connecting element for the cells 1 consists of a frame 12, which is provided with apertures 13 to receive the cells 1. The apertures 13 have different spacings from one another, so as to correspond to the spacings of the cell wells 11 in the cell holder 9. The cell wells 11 can be provided with arrangements for heating and cooling the cells (not shown).

Additional advantages and modifications will readily occur to those skilled in the art. Therefore, the invention in its broader aspects is not limited to the specific details, representative devices, and illustrative examples shown an described. Accordingly, departures may be made from such details without departing from the spirit or scope of the general inventive concept as defined by the appended claims and their equivalents.

What is claimed:

1. A cell arrangement for optical investigations, comprising a cell holder for receiving a plurality of cells of the cell arrangement, wherein said plurality of cells are arranged in strips in which the individual cells are held at different spacings from one another by connecting elements to form a single unambiguously defined configuration, and said cell holder is provided with cell wells which are disposed in sequence and the spacings of which correspond to said single unambiguously defined configuration of the cells so that the cells may only be inserted in said cell holder in said configuration.

2. The cell arrangement as in claim 1, wherein the connecting elements consists of a frame provided with apertures, the apertures having different spacings from one another to correspond to said spacing of said cells wells.

3. The cell arrangement as in claim 1, wherein the connecting elements consist of webs of different width.

4. The cell arrangement as in claim 3, wherein said webs are disposed parallel to a longitudinal axis of said cells.

5. The cell arrangement as in claim 3, wherein the webs are configured with predetermined breaking points.

* * * * *